US008710152B2

(12) United States Patent
Farcet et al.

(10) Patent No.: US 8,710,152 B2
(45) Date of Patent: Apr. 29, 2014

(54) BLOCK POLYMERS AND THEIR PROCESS OF PREPARATION

(75) Inventors: Céline Farcet, Paris (FR); Bertrand Lion, Paris (FR)

(73) Assignee: L'Oreal, Paris (FR)

( * ) Notice: Subject to any disclaimer, the term of this patent is extended or adjusted under 35 U.S.C. 154(b) by 24 days.

(21) Appl. No.: 11/878,849

(22) Filed: Jul. 27, 2007

(65) Prior Publication Data

US 2008/0031837 A1    Feb. 7, 2008

Related U.S. Application Data

(60) Provisional application No. 60/835,907, filed on Aug. 7, 2006.

(30) Foreign Application Priority Data

Jul. 27, 2006  (FR) ..................... 06 53144

(51) Int. Cl.
| | |
|---|---|
| *C08F 265/06* | (2006.01) |
| *A61K 8/72* | (2006.01) |
| *A61K 8/90* | (2006.01) |
| *A61K 8/81* | (2006.01) |
| *C08F 18/02* | (2006.01) |

(52) U.S. Cl.
USPC ............. 525/299; 525/242; 525/298; 424/64; 424/70.11; 424/78.03

(58) Field of Classification Search
USPC ......... 525/191, 202, 210, 216, 222, 242, 289, 525/298, 299, 301, 302, 308, 309; 524/242, 524/289, 299, 301, 302; 424/64, 70.11, 424/78.03

See application file for complete search history.

(56) References Cited

U.S. PATENT DOCUMENTS

| | | | |
|---|---|---|---|
| 2,047,398 | A | 7/1936 | Voss et al. |
| 2,528,378 | A | 10/1950 | Mannheimer et al. |
| 2,723,248 | A | 11/1955 | Wright |
| 2,781,354 | A | 2/1957 | Mannheimer et al. |
| 3,673,160 | A | 6/1972 | Buisson et al. |
| 3,716,633 | A | 2/1973 | Viout et al. |
| 3,802,841 | A | 4/1974 | Robin |
| 3,836,537 | A | 9/1974 | Boerwinkle et al. |
| 3,910,862 | A | 10/1975 | Barabas et al. |
| 3,915,921 | A | 10/1975 | Schlatzer et al. |
| 3,925,542 | A | 12/1975 | Viout et al. |
| 3,937,811 | A | 2/1976 | Papantoniou et al. |
| 3,946,749 | A | 3/1976 | Papantoniou |
| 3,966,403 | A | 6/1976 | Papantoniou et al. |
| 3,966,404 | A | 6/1976 | Papantoniou et al. |
| 3,990,459 | A | 11/1976 | Papantoniou |
| 4,030,512 | A | 6/1977 | Papantoniou et al. |
| 4,031,307 | A | 6/1977 | DeMartino et al. |
| 4,032,628 | A | 6/1977 | Papantoniou et al. |
| 4,070,533 | A | 1/1978 | Papantoniou et al. |
| 4,076,912 | A | 2/1978 | Papantoniou et al. |
| RE29,871 | E | 12/1978 | Papantoniou et al. |
| 4,128,631 | A | 12/1978 | Lundmark et al. |
| 4,129,711 | A | 12/1978 | Viout et al. |
| 4,131,576 | A | 12/1978 | Iovine |
| 4,137,208 | A | 1/1979 | Elliott |
| 4,152,416 | A | 5/1979 | Spitzer et al. |
| 4,165,367 | A | 8/1979 | Chakrabarti |
| 4,223,009 | A | 9/1980 | Chakrabarti |
| 4,282,203 | A | 8/1981 | Jacquet et al. |
| 4,289,752 | A | 9/1981 | Mahieu et al. |
| 4,425,326 | A | 1/1984 | Guillon et al. |
| 4,509,949 | A | 4/1985 | Huang et al. |
| 4,693,935 | A | 9/1987 | Mazurek |
| 4,728,571 | A | 3/1988 | Clemens et al. |
| 4,887,622 | A | 12/1989 | Gueret |
| 4,972,037 | A | 11/1990 | Garbe et al. |
| 4,981,902 | A | 1/1991 | Mitra et al. |
| 4,981,903 | A | 1/1991 | Garbe et al. |
| 5,000,937 | A | 3/1991 | Grollier et al. |

(Continued)

FOREIGN PATENT DOCUMENTS

| | | |
|---|---|---|
| DE | 2 330 956 | 1/1974 |
| DE | 100 22 247 | 11/2001 |

(Continued)

OTHER PUBLICATIONS

French Search Report for FR 0653144, dated Feb. 13, 2007.
Response filed Mar. 10, 2009, in co-pending U.S. Appl. No. 10/528,698.
Aldrich: Polymer Properties; 4th Ed. Catalog No. Z41, 247-3 (1999) published by John Wiley, New York.
Boutevin, B. et al., "Study of Morphological and Mechanical Properties of PP/PBT," Polymer Bulletin, 34, pp. 117-123, (1995).
Buzin, A. et al., "Calorimetric Study of Block-Copolymers of Poly(n-butyl Acrylate) and Gradient Poly(n-butyl acrylate-co-methyl methacrylate)" vol. 43, 2002, pp. 5563-5569.
Co-pending U.S. Appl. No. 10/528,698, filed Mar. 22, 2005; Inventors: Veronique Ferrari et al.

(Continued)

*Primary Examiner* — Irina S Zemel
*Assistant Examiner* — Jeffrey Lenihan
(74) *Attorney, Agent, or Firm* — Novak Druce Connolly Bove + Quigg LLP

(57) ABSTRACT

Disclosed herein are novel block polymers comprising at least one first block and at least one second block, wherein the at least one first block comprises at least one acrylate monomer of formula $CH_2\!=\!CH\!-\!COOR_2$ wherein $R_2$ is chosen from $C_4$ to $C_{12}$ cycloalkyl groups and at least one methacrylate monomer of formula $CH_2\!=\!C(CH_3)\!-\!COOR'_2$ wherein $R'_2$ is chosen from $C_4$ to $C_{12}$ cycloalkyl groups, and the second block comprises at least one acrylic acid monomer and at least one monomer with a glass transition temperature of less than or equal to 20° C. Also disclosed herein is a process for the preparation of such polymers which may be carried out continuously in a single reactor. Finally, further disclosed herein are compositions comprising the novel polymers and processes using the composition for making up and/or caring for keratinous substances or for improving the hold of a cosmetic composition while maintaining its gloss.

18 Claims, No Drawings

(56) References Cited

U.S. PATENT DOCUMENTS

| | | |
|---|---|---|
| 5,061,481 A | 10/1991 | Suzuki et al. |
| 5,110,582 A | 5/1992 | Hungerbuhler et al. |
| 5,156,911 A | 10/1992 | Stewart |
| 5,209,924 A | 5/1993 | Garbe et al. |
| 5,219,560 A | 6/1993 | Suzuki et al. |
| 5,266,321 A | 11/1993 | Shukuzaki |
| 5,362,485 A | 11/1994 | Hayama et al. |
| 5,391,631 A | 2/1995 | Porsch et al. |
| 5,468,477 A | 11/1995 | Kumar et al. |
| 5,472,798 A | 12/1995 | Kumazawa et al. |
| 5,491,865 A | 2/1996 | Gueret |
| 5,492,426 A | 2/1996 | Gueret |
| 5,519,063 A | 5/1996 | Mondet et al. |
| 5,538,717 A | 7/1996 | De La Poterie |
| 5,681,877 A | 10/1997 | Hosotte-Filbert et al. |
| 5,686,067 A | 11/1997 | Shih et al. |
| 5,690,918 A | 11/1997 | Jacks et al. |
| 5,711,940 A | 1/1998 | Kuentz et al. |
| 5,725,882 A | 3/1998 | Kumar et al. |
| 5,736,125 A | 4/1998 | Morawsky et al. |
| 5,747,013 A | 5/1998 | Mougin et al. |
| 5,756,635 A | 5/1998 | Michaud et al. |
| 5,772,347 A | 6/1998 | Gueret |
| 5,783,657 A | 7/1998 | Pavlin et al. |
| 5,807,540 A | 9/1998 | Junino et al. |
| 5,849,275 A | 12/1998 | Calello et al. |
| 5,849,318 A | 12/1998 | Imai et al. |
| 5,879,095 A | 3/1999 | Gueret |
| 5,897,870 A | 4/1999 | Schehlmann et al. |
| 5,948,393 A | 9/1999 | Tomomasa et al. |
| 5,994,446 A | 11/1999 | Graulus et al. |
| 6,001,367 A | 12/1999 | Bazin et al. |
| 6,001,374 A | 12/1999 | Nichols |
| 6,027,739 A | 2/2000 | Nichols |
| 6,033,650 A | 3/2000 | Calello et al. |
| 6,059,473 A | 5/2000 | Gueret |
| 6,074,654 A | 6/2000 | Drechsler et al. |
| 6,083,516 A | 7/2000 | Curtis et al. |
| 6,106,813 A | 8/2000 | Mondet et al. |
| 6,106,820 A | 8/2000 | Morrissey et al. |
| 6,120,781 A | 9/2000 | Le Bras et al. |
| 6,126,929 A | 10/2000 | Mougin |
| 6,132,742 A | 10/2000 | Le Bras et al. |
| 6,139,849 A | 10/2000 | Lesaulnier et al. |
| 6,140,431 A | 10/2000 | Kinker et al. |
| 6,153,206 A | 11/2000 | Anton et al. |
| 6,156,804 A | 12/2000 | Chevalier et al. |
| 6,160,054 A | 12/2000 | Schwindeman et al. |
| 6,165,457 A | 12/2000 | Midha et al. |
| 6,166,093 A | 12/2000 | Mougin et al. |
| 6,174,968 B1 | 1/2001 | Hoxmeier |
| 6,180,123 B1 | 1/2001 | Mondet |
| 6,197,883 B1 | 3/2001 | Schimmel et al. |
| 6,225,390 B1 | 5/2001 | Hoxmeier |
| 6,228,946 B1 | 5/2001 | Kitayama et al. |
| 6,228,967 B1 | 5/2001 | Fost et al. |
| 6,238,679 B1 | 5/2001 | De La Poterie et al. |
| 6,254,878 B1 | 7/2001 | Bednarek et al. |
| 6,258,916 B1 | 7/2001 | Michaud et al. |
| 6,267,951 B1 | 7/2001 | Shah et al. |
| 6,268,466 B1 | 7/2001 | MacQueen et al. |
| 6,280,713 B1 | 8/2001 | Tranchant et al. |
| 6,303,105 B1 | 10/2001 | Shah et al. |
| 6,319,959 B1 | 11/2001 | Mougin et al. |
| 6,326,011 B1 | 12/2001 | Miyazawa et al. |
| 6,328,495 B1 | 12/2001 | Gueret |
| 6,342,237 B1 | 1/2002 | Bara |
| 6,372,876 B1 | 4/2002 | Kim et al. |
| 6,386,781 B1 | 5/2002 | Gueret |
| 6,395,265 B1 | 5/2002 | Mougin et al. |
| 6,399,691 B1 | 6/2002 | Melchiors et al. |
| 6,410,005 B1 | 6/2002 | Galleguillos et al. |
| 6,410,666 B1 | 6/2002 | Grubbs et al. |
| 6,412,496 B1 | 7/2002 | Gueret |
| 6,423,306 B2 | 7/2002 | Caes et al. |
| 6,464,969 B2 | 10/2002 | De La Poterie et al. |
| 6,484,731 B1 | 11/2002 | Lacout |
| 6,491,927 B1 | 12/2002 | Arnaud et al. |
| 6,518,364 B2 | 2/2003 | Charmot et al. |
| 6,531,535 B2 | 3/2003 | Melchiors et al. |
| 6,552,146 B1 | 4/2003 | Mougin |
| 6,581,610 B1 | 6/2003 | Gueret |
| 6,649,173 B1 | 11/2003 | Arnaud et al. |
| 6,663,855 B2 | 12/2003 | Frechet et al. |
| 6,663,885 B1 | 12/2003 | Hager et al. |
| 6,685,925 B2 | 2/2004 | Frechet et al. |
| 6,692,173 B2 | 2/2004 | Gueret |
| 6,692,733 B1 | 2/2004 | Mougin |
| 6,770,271 B2 | 8/2004 | Mondet et al. |
| 6,805,872 B2 | 10/2004 | Mougin |
| 6,833,419 B2 | 12/2004 | Morschhauser et al. |
| 6,843,611 B2 | 1/2005 | Blondeel et al. |
| 6,866,046 B2 | 3/2005 | Gueret |
| 6,881,780 B2 | 4/2005 | Bryant et al. |
| 6,890,522 B2 | 5/2005 | Frechet et al. |
| 6,891,011 B2 | 5/2005 | Morschhauser et al. |
| 6,905,696 B2 | 6/2005 | Marotta et al. |
| 6,946,518 B2 | 9/2005 | De La Poterie |
| 6,960,339 B1 | 11/2005 | Ferrari |
| 6,964,995 B2 | 11/2005 | Morschhauser et al. |
| 7,022,791 B2 | 4/2006 | Loffler et al. |
| 7,025,973 B2 | 4/2006 | Loffler et al. |
| 7,053,146 B2 | 5/2006 | Morschhauser et al. |
| 7,081,507 B2 | 7/2006 | Morschhauser et al. |
| 7,144,171 B2 | 12/2006 | Blondeel et al. |
| 7,151,137 B2 | 12/2006 | Morschhauser et al. |
| 7,176,170 B2 | 2/2007 | Dubief et al. |
| 7,186,405 B2 | 3/2007 | Loeffler et al. |
| 7,186,774 B2 | 3/2007 | Morschhauser et al. |
| 7,244,421 B2 | 7/2007 | Loffler et al. |
| 7,279,154 B2 | 10/2007 | Loffler et al. |
| 7,297,328 B2 | 11/2007 | Loffler et al. |
| 7,332,155 B2 | 2/2008 | Loffler et al. |
| 7,358,303 B2 | 4/2008 | De La Poterie |
| 7,393,520 B2 | 7/2008 | Loeffler et al. |
| 7,399,478 B2 | 7/2008 | Loeffler et al. |
| 2002/0015611 A1 | 2/2002 | Blondeel et al. |
| 2002/0018759 A1 | 2/2002 | Pagano et al. |
| 2002/0020424 A1 | 2/2002 | Gueret |
| 2002/0035237 A1 | 3/2002 | Lawson et al. |
| 2002/0054783 A1 | 5/2002 | Gueret |
| 2002/0055562 A1 | 5/2002 | Butuc |
| 2002/0061319 A1 | 5/2002 | Bernard et al. |
| 2002/0064539 A1 | 5/2002 | Philippe et al. |
| 2002/0076390 A1 | 6/2002 | Kantner et al. |
| 2002/0076425 A1 | 6/2002 | Mondet et al. |
| 2002/0098217 A1 | 7/2002 | Piot et al. |
| 2002/0115780 A1 | 8/2002 | Mougin |
| 2002/0150546 A1 | 10/2002 | Mougin et al. |
| 2002/0151638 A1 | 10/2002 | Melchiors et al. |
| 2002/0159965 A1 | 10/2002 | Frechet et al. |
| 2002/0160026 A1 | 10/2002 | Frechet et al. |
| 2003/0003154 A1 | 1/2003 | De La Poterie |
| 2003/0017124 A1 | 1/2003 | Agostini et al. |
| 2003/0017182 A1 | 1/2003 | Tournilhac |
| 2003/0021815 A9 | 1/2003 | Mondet et al. |
| 2003/0024074 A1 | 2/2003 | Hartman |
| 2003/0039621 A1 | 2/2003 | Arnaud et al. |
| 2003/0059392 A1 | 3/2003 | L'Alloret |
| 2003/0113285 A1 | 6/2003 | Meffert et al. |
| 2003/0124074 A1 | 7/2003 | Mougin et al. |
| 2003/0124079 A1 | 7/2003 | Mougin et al. |
| 2003/0185774 A1 | 10/2003 | Dobbs et al. |
| 2003/0191271 A1 | 10/2003 | Mondet et al. |
| 2004/0009136 A1 | 1/2004 | Dubief et al. |
| 2004/0013625 A1 | 1/2004 | Kanji |
| 2004/0014872 A1 | 1/2004 | Raether |
| 2004/0039101 A1 | 2/2004 | Dubief et al. |
| 2004/0052745 A1 | 3/2004 | Bernard et al. |
| 2004/0052752 A1 | 3/2004 | Samain et al. |
| 2004/0077788 A1 | 4/2004 | Guerra et al. |
| 2004/0091444 A1 | 5/2004 | Loffler et al. |
| 2004/0093676 A1 | 5/2004 | Vidal et al. |
| 2004/0096409 A1 | 5/2004 | Loeffler et al. |

(56) References Cited

U.S. PATENT DOCUMENTS

| | | |
|---|---|---|
| 2004/0096411 A1 | 5/2004 | Frechet et al. |
| 2004/0097657 A1 | 5/2004 | Morschhauser et al. |
| 2004/0109835 A1 | 6/2004 | Loffler et al. |
| 2004/0109836 A1 | 6/2004 | Loffler et al. |
| 2004/0109838 A1 | 6/2004 | Morschhauser et al. |
| 2004/0115148 A1 | 6/2004 | Loffler et al. |
| 2004/0115149 A1 | 6/2004 | Loffler et al. |
| 2004/0115157 A1 | 6/2004 | Loffler et al. |
| 2004/0116628 A1 | 6/2004 | Morschhauser et al. |
| 2004/0116634 A1 | 6/2004 | Morschhauser et al. |
| 2004/0120906 A1 | 6/2004 | Toumi et al. |
| 2004/0120920 A1 | 6/2004 | Lion et al. |
| 2004/0137020 A1 | 7/2004 | De La Poterie et al. |
| 2004/0137021 A1 | 7/2004 | De La Poterie et al. |
| 2004/0141937 A1 | 7/2004 | Loffler et al. |
| 2004/0141943 A1 | 7/2004 | Mougin et al. |
| 2004/0142831 A1 | 7/2004 | Jager Lezer |
| 2004/0167304 A1 | 8/2004 | Morschhauser et al. |
| 2004/0223933 A1 | 11/2004 | Hiwatashi et al. |
| 2004/0241118 A1 | 12/2004 | Simon et al. |
| 2005/0002724 A1 | 1/2005 | Blondeel et al. |
| 2005/0020779 A1 | 1/2005 | Mougin et al. |
| 2005/0032998 A1 | 2/2005 | Morschhauser et al. |
| 2005/0089536 A1 | 4/2005 | Loffler et al. |
| 2005/0095213 A1 | 5/2005 | Blin et al. |
| 2005/0106197 A1 | 5/2005 | Blin et al. |
| 2005/0129641 A1 | 6/2005 | Arnaud et al. |
| 2005/0201958 A1 | 9/2005 | De La Poterie |
| 2005/0220747 A1 | 10/2005 | Lion et al. |
| 2005/0232887 A1 | 10/2005 | Morschhauser et al. |
| 2005/0287103 A1 | 12/2005 | Filippi et al. |
| 2006/0093568 A1 | 5/2006 | Blin et al. |
| 2006/0099164 A1 | 5/2006 | De La Poterie et al. |
| 2006/0099231 A1 | 5/2006 | De La Poterie et al. |
| 2006/0115444 A1 | 6/2006 | Blin et al. |
| 2006/0127334 A1 | 6/2006 | Ferrari et al. |
| 2006/0134032 A1 | 6/2006 | Ilekti et al. |
| 2006/0134038 A1 | 6/2006 | De La Poterie et al. |
| 2006/0134044 A1 | 6/2006 | Blin et al. |
| 2006/0134051 A1 | 6/2006 | Blin et al. |
| 2006/0147402 A1 | 7/2006 | Blin et al. |
| 2006/0147403 A1 | 7/2006 | Ferrari et al. |
| 2007/0003506 A1 | 1/2007 | Mougin et al. |
| 2007/0003507 A1 | 1/2007 | Mougin et al. |
| 2007/0166259 A1* | 7/2007 | Vicic et al. ................ 424/70.11 |
| 2008/0014232 A1 | 1/2008 | Arnaud et al. |
| 2008/0050329 A1 | 2/2008 | De La Poterie |
| 2008/0069793 A1 | 3/2008 | Loffler et al. |
| 2008/0107617 A1 | 5/2008 | Loffler et al. |
| 2008/0159965 A1 | 7/2008 | Mougin et al. |
| 2008/0207773 A1 | 8/2008 | Loffler et al. |
| 2008/0219943 A1 | 9/2008 | De La Poterie |

FOREIGN PATENT DOCUMENTS

| | | |
|---|---|---|
| DE | 100 29 697 | 12/2001 |
| EP | 1 279 398 | 9/1971 |
| EP | 0 080 976 | 6/1983 |
| EP | 0 295 886 | 12/1988 |
| EP | 0 320 218 | 6/1989 |
| EP | 0 173 109 | 10/1989 |
| EP | 0 388 582 | 9/1990 |
| EP | 0 412 704 | 2/1991 |
| EP | 0 412 707 | 2/1991 |
| EP | 0 549 494 | 6/1993 |
| EP | 0 582 152 | 2/1994 |
| EP | 0 216 479 | 8/1994 |
| EP | 0 619 111 | 10/1994 |
| EP | 0 637 600 | 2/1995 |
| EP | 0 648 485 | 4/1995 |
| EP | 0 656 021 | 6/1995 |
| EP | 0 667 146 | 8/1995 |
| EP | 0 550 745 | 9/1995 |
| EP | 0 686 858 | 12/1995 |
| EP | 0 750 031 | 12/1996 |
| EP | 0 751 162 | 1/1997 |
| EP | 0 751 170 | 1/1997 |
| EP | 0 815 836 | 1/1998 |
| EP | 0 847 752 | 6/1998 |
| EP | 0 861 859 | 9/1998 |
| EP | 0 951 897 | 10/1999 |
| EP | 1 018 311 | 7/2000 |
| EP | 1 024 184 | 8/2000 |
| EP | 1 043 345 | 10/2000 |
| EP | 1 066 817 | 1/2001 |
| EP | 1 068 856 | 1/2001 |
| EP | 1 082 953 | 3/2001 |
| EP | 1 159 950 | 12/2001 |
| EP | 1 192 930 | 4/2002 |
| EP | 1 201 221 | 5/2002 |
| EP | 1 356 799 | 10/2003 |
| EP | 1 366 741 | 12/2003 |
| EP | 1 366 744 | 12/2003 |
| EP | 1 366 746 | 12/2003 |
| EP | 1 411 069 A2 | 4/2004 |
| EP | 0 955 039 | 5/2004 |
| EP | 1 421 928 A2 | 5/2004 |
| EP | 1 440 680 | 7/2004 |
| EP | 1 518 534 A2 | 3/2005 |
| EP | 1 518 535 A1 | 3/2005 |
| EP | 1 604 634 | 12/2005 |
| FK | 2 816 503 | 5/2002 |
| FR | 1 222 944 | 6/1960 |
| FR | 1 400 366 | 4/1965 |
| FR | 1 564 110 | 3/1969 |
| FR | 1 580 545 | 9/1969 |
| FR | 2 077 143 | 9/1971 |
| FR | 2 079 785 | 11/1971 |
| FR | 2 140 977 | 1/1973 |
| FR | 2 232 303 | 1/1975 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 2 710 552 | 4/1995 |
| FR | 2 710 646 | 4/1995 |
| FR | 2 722 380 | 6/1996 |
| FR | 2 727 609 | 6/1996 |
| FR | 2 743 297 | 7/1997 |
| FR | 2 761 959 | 10/1998 |
| FR | 2 796 529 | 7/1999 |
| FR | 2 775 566 | 9/1999 |
| FR | 2 775 593 | 9/1999 |
| FR | 2 791 042 | 9/2000 |
| FR | 2 791 987 | 10/2000 |
| FR | 2 791 988 | 10/2000 |
| FR | 2 792 190 | 10/2000 |
| FR | 2 792 618 | 10/2000 |
| FR | 2 798 061 | 3/2001 |
| FR | 2 803 743 | 7/2001 |
| FR | 2 806 273 | 9/2001 |
| FR | 2 296 402 | 11/2001 |
| FR | 2 809 306 | 11/2001 |
| FR | 2 811 993 | 1/2002 |
| FR | 2 814 365 | 3/2002 |
| FR | 2 823 101 | 10/2002 |
| FR | 2 823 103 | 10/2002 |
| FR | 2 827 514 | 1/2003 |
| FR | 2 831 430 | 5/2003 |
| FR | 2 832 719 | 5/2003 |
| FR | 2 832 720 | 5/2003 |
| FR | 2 834 458 | 7/2003 |
| FR | 2 840 205 | 12/2003 |
| FR | 2 840 209 | 12/2003 |
| FR | 2 842 417 | 1/2004 |
| FR | 2 844 709 | 3/2004 |
| FR | 2 860 143 | 4/2005 |
| FR | 2 860 156 | 4/2005 |
| FR | 2 880 268 | 7/2006 |
| GB | 0 839 805 | 6/1960 |
| GB | 0 922 457 | 4/1963 |

(56) References Cited

FOREIGN PATENT DOCUMENTS

| | | |
|---|---|---|
| GB | 1 021 400 | 3/1966 |
| GB | 1 169 862 | 11/1969 |
| GB | 1 324 745 | 7/1973 |
| GB | 1 331 819 | 9/1973 |
| GB | 1 407 659 | 9/1975 |
| GB | 1 572 626 | 7/1980 |
| JP | 5-221829 | 8/1993 |
| JP | 06-279323 | 10/1994 |
| JP | 07-196450 | 8/1995 |
| JP | 07-309721 | 11/1995 |
| JP | 07-324017 | 12/1995 |
| JP | 08-119836 | 5/1996 |
| JP | 09-263518 | 10/1997 |
| JP | 10-506404 | 6/1998 |
| JP | 11-100307 | 4/1999 |
| JP | 11-124312 | 5/1999 |
| JP | 2000-83728 | 3/2000 |
| JP | 2000-319325 | 11/2000 |
| JP | 2000-319326 | 11/2000 |
| JP | 2001-348553 | 12/2001 |
| JP | 2001-527559 | 12/2001 |
| JP | 2002-201110 | 7/2002 |
| JP | 2002-201244 | 7/2002 |
| JP | 2003-40336 | 2/2003 |
| JP | 2003-73222 | 3/2003 |
| JP | 2003-081742 | 3/2003 |
| JP | 2003-286142 | 10/2003 |
| JP | 2004-002432 | 1/2004 |
| JP | 2004-002435 | 1/2004 |
| JP | 2004-149772 | 5/2004 |
| JP | 2004-269497 | 9/2004 |
| JP | 2005-104979 | 4/2005 |
| JP | 2006-503921 | 3/2006 |
| JP | 2006-507355 | 3/2006 |
| JP | 2006-507365 | 3/2006 |
| JP | 2006-507366 | 3/2006 |
| JP | 2006-507367 | 3/2006 |
| JP | 2006-151867 | 6/2006 |
| LU | 75370 | 7/1976 |
| LU | 75371 | 7/1976 |
| WO | WO 93/01797 | 2/1993 |
| WO | WO 93/23009 | 11/1993 |
| WO | WO 93/23446 | 11/1993 |
| WO | WO 94/03510 | 2/1994 |
| WO | WO 95/00578 | 1/1995 |
| WO | WO 95/03776 | 2/1995 |
| WO | WO 95/06078 | 3/1995 |
| WO | WO 96/10044 | 4/1996 |
| WO | WO 97/17057 | 5/1997 |
| WO | WO 98/31329 | 7/1998 |
| WO | WO 98/38981 | 9/1998 |
| WO | WO 98/42298 | 10/1998 |
| WO | WO 98/44012 | 10/1998 |
| WO | WO 98/51276 | 11/1998 |
| WO | WO 00/26285 | 5/2000 |
| WO | WO 00/28948 | 5/2000 |
| WO | WO 00/40216 | 7/2000 |
| WO | WO 00/49997 | 8/2000 |
| WO | WO 01/03538 | 1/2001 |
| WO | WO 01/13863 | 3/2001 |
| WO | WO 01/19333 | 3/2001 |
| WO | WO 01/30886 | 5/2001 |
| WO | WO 01/43703 | 6/2001 |
| WO | WO 01/51018 | 7/2001 |
| WO | WO 01/89470 | 11/2001 |
| WO | WO 01/95871 | 12/2001 |
| WO | WO 02/05762 | 1/2002 |
| WO | WO 02/05765 | 1/2002 |
| WO | WO 02/28358 | 4/2002 |
| WO | WO 02/34218 | 5/2002 |
| WO | WO 02/067877 | 9/2002 |
| WO | WO 02/080869 | 10/2002 |
| WO | WO 03/018423 | 3/2003 |
| WO | WO 03/046032 | 6/2003 |
| WO | WO 03/046033 | 6/2003 |
| WO | WO 2004/022009 | 3/2004 |
| WO | WO 2004/022010 | 3/2004 |
| WO | WO 2004/024700 | 3/2004 |
| WO | WO 2004/028485 | 4/2004 |
| WO | WO 2004/028487 | 4/2004 |
| WO | WO 2004/028489 | 4/2004 |
| WO | WO 2004/028491 | 4/2004 |
| WO | WO-2005030158 A1 * | 4/2005 |

OTHER PUBLICATIONS

Co-pending U.S. Appl. No. 10/528,699, filed Mar. 22, 2005; Inventors: Philippe Ilekti et al.
Co-pending U.S. Appl. No. 10/528,835, filed Mar. 23, 2005; Inventors: Xavier Blin et al.
Co-pending U.S. Appl. No. 10/529,218, filed Mar. 25, 2005; Inventors: Xavier Blin et al.
Co-pending U.S. Appl. No. 10/529,264, filed Mar. 25, 2005; Inventors: Veronique Ferrari et al.
Co-pending U.S. Appl. No. 10/529,265, filed Sep. 28, 2005; Inventors: Xavier Blin et al.
Co-pending U.S. Appl. No. 10/529,266, filed Mar. 25, 2005; Inventors: Xavier Blin et al.
Co-pending U.S. Appl. No. 10/529,267, filed Sep. 29, 2005; Inventors: Valerie De La Poterie et al.
Co-pending U.S. Appl. No. 10/529,318, filed Mar. 25, 2005; Inventors: Xavier Blin et al.
Co-pending U.S. Appl. No. 10/573,579; filed Dec. 26, 2006; Inventor: Marco Vicic et al.
Co-pending U.S. Appl. No. 10/585,817, filed Jan. 10, 2007; Inventor: Valerie De La Poterie.
Co-pending U.S. Appl. No. 10/585,818, filed Jul. 12, 2006; Inventors: Valerie De La Poterie.
Co-pending U.S. Appl. No. 10/670,388, filed Sep. 26, 2003; Inventors: Beatrice Toumi et al.
Co-pending U.S. Appl. No. 10/670,478, filed Sep. 26, 2003; Inventors: Bertrand Lion et al.
Co-pending U.S. Appl. No. 10/949,435, filed Sep. 27, 2004; Inventors: Xavier Blin et al.
Co-pending U.S. Appl. No. 10/949,448, filed Sep. 27, 2004; Inventors: Xavier Blin et al.
Co-pending U.S. Appl. No. 11/086,906, filed Mar. 23, 2005; Inventors: Philippe Ilekti et al.
Co-pending U.S. Appl. No. 11/089,210, filed Mar. 25, 2005.
Co-pending U.S. Appl. No. 11/858,994, filed Sep. 21, 2007; Inventors: Bertrand Lion et al.
Co-pending U.S. Appl. No. 11/859,004, filed Sep. 21, 2007; Inventors: Bertrand Lion et al.
Co-pending U.S. Appl. No. 11/859,015, filed Sep. 21, 2007; Inventors: Bertrand Lion et al.
Co-pending U.S. Appl. No. 11/878,067, filed Jul. 20, 2007; Inventors: Caroline Lebre et al.
Cortazar, M. et al., "Glass Transition Temperatures of Plasticized Polyarylate,", Polymer Bulletin 18, 149-154 (1987).
English Derwent Abstract for EP 1 082 953, dated Mar. 14, 2001.
English Derwent Abstract for EP 1 159 950, dated Dec. 5, 2001.
English Derwent Abstract for FR 2 798 061, dated Mar. 9, 2001.
English Derwent Abstract for FR 2 803 743, dated Jul. 20, 2001.
English Derwent Abstract for FR 2 832 719, dated May 30, 2003.
English Derwent Abstract for WO 01/03538, dated Jan. 18, 2001.
English Derwent Abstract for WO 04/028489, dated Apr. 8, 2004.
English language Abstract of FR 2 357 241, dated Feb. 3, 1978.
English language Abstract of FR 2 710 552, dated Apr. 7, 1995.
English language Abstract of FR 2 710 646, dated Apr. 7, 1995.
English language Abstract of FR 2 791 987, dated Oct. 13, 2000.
English language Abstract of FR 2 832 720, dated May 30, 2003.
English language Abstract of FR 2 834 458, dated Jul. 11, 2003.
English language Abstract of FR 2 880 268, dated Jul. 7, 2006.
English language Abstract of JP 07-309721, dated Nov. 28, 1995.
English language Abstract of JP 08-119836, dated May 14, 1996.
English language Abstract of JP 2003-40336, Feb. 13, 2003.
English language Abstract of JP 2006-151867, dated Jun. 15, 2006.
English language Abstract of WO 01/13863, dated Mar. 1, 2001.
English language Abstract of WO 01/51018, dated Jul. 19, 2001.

(56) References Cited

OTHER PUBLICATIONS

English language Derwent Abstract for EP 0 080 976, dated Jun. 8, 1983.
English language Derwent Abstract for FR 2 775 566, dated Sep. 10, 1999.
English language Derwent Abstract for FR 2 792 190, dated Oct. 20, 2000.
English language Derwent Abstract for FR 2 831 430, dated May 2, 2003.
English language Derwent Abstract for JP 06-279323, dated Oct. 4, 1994.
English language Derwent Abstract for JP 07-196450, dated Aug. 1, 1995.
English language Derwent Abstract for JP 09-263518, dated Oct. 7, 1997.
English language Derwent Abstract for JP 11-124312, dated May 11, 1999.
English language Derwent Abstract of EP 0 648 485, dated Apr. 19, 1995.
English language Derwent Abstract of FR 2 140 977, dated Jan. 19, 1973.
English language Derwent Abstract of FR 2 860 156, Apr. 1, 2005.
English language Derwent Abstract of JP 11-100307, Apr. 13, 1999.
English language Derwent Abstract of JP 2001-348553, Dec. 18, 2001.
English language Derwent Abstract of JP 2002-201244, dated Jul. 19, 2002.
English language Derwent Abstract of JP 2004-002432, Jan. 8, 2004.
English language Derwent Abstract of JP 2004-002435, Jan. 8, 2004.
English language Derwent Abstract of JP 5-221829, dated Aug. 31, 1993.
Erichsen, J. et al., "Molecular Weight Dependence of the Surface Glass Transition of Polystyrene Films Investigated by the Embedding of Gold Nanoclusters," MRS Publication, 2001.
European Search Report for EP 03 29 2383, dated May 17, 2004, in Co-pending U.S. Appl. No. 10/670,388.
Flick, "Cosmetic Additives: An Industrial Guide", Noyes Publications, Park Ridge, NJ, p. 266 (1991).
Fonnum, et al., Colloid Polym. Sci., 1993, 271: 380-389.
French Search Report for FR 02/11949 for Copending U.S. Appl. No. 10/670,478, dated Jul. 7, 2003.
French Search Report for FR 03/11340 for Copending U.S. Appl. No. 10/949,448, dated May 9, 2005.
French Search Report for FR 04/03088, dated Nov. 2, 2004.
French Search Report for FR 04/03090, dated Sep. 30, 2004.
French Search Report for FR 04/50572, for Copending U.S. Appl. No. 11/086,906, dated Nov. 9, 2004.
French Search Report for FR 06/53154, dated Apr. 2, 2007.
Hamley, I.W., "Crystallization in Block Copolymers," Advances in Polymer Science, vol. 148, pp. 113-137 (1999).
Hansen, C.M., "The Three Dimensional Solubility Parameter—Key to Paint Component Affinities: I. Solvents, Plasticizers, Polymers, and Resins", Journal of Paint Technology, vol. 39. No. 505, pp. 104-117 (1967).
HCAPLUS abstract 1964: 70247, abstracting: Develop. Ind. Microbiol., vol. 2, pp. 47-53 (1961).
International Search Report for PCT Application No. PCT/FR03/02849 (PCt counterpart for U.S. Appl. No. 10/529,265), dated Jun. 24, 2004.
International Search Report for PCT/FR03/002844 (Priority Application for U.S. Appl. No. 10/529,318), dated May 14, 2005.
International Search Report for PCT/FR03/002847 (Priority Application for U.S. Appl. No. 10/529,266), dated May 17, 2004.
International Search Report for PCT/FR03/02841 (PCT counterpart for U.S. Appl. No. 10/529,267), dated Jun. 1, 2004.
International Search Report for PCT/FR03/02842 (Priority Application for U.S. Appl. No. 10/529,218), dated May 17, 2004.
International Search Report for PCT/FR03/02843 (Priority Application for U.S, Appl. No. 10/528,698), dated May 17, 2004.
International Search Report for PCT/FR03/02845 (Priority Application for U.S. Appl. No. 10/529,264), dated May 17, 2004.
International Search Report for PCT/FR03/02846 (Priority Application for U.S. Appl. No. 10/528,699), dated May 17, 2004.
International Search Report for PCT/FR03/02848 (Priority Application for U.S. Appl. No. 10/528,835), dated May 17, 2004.
International Search Report for PCT/IB2005/000230 (PCT counterpart for U.S. Appl. No. 10/585,817), dated May 27, 2005.
International Search Report for PCT/IB2005/000236 (PCT counterpart for U.S. Appl. No. 10/585,818), dated Aug. 3, 2005.
Kirk-Othmer, "Encyclopedia of Chemical Technology", vol. 22, 3rd Edition, Wiley, 1979, pp. 333-432.
Nojima. S., "Melting Behavior of Poly (E-caprolactone)-block-polybutadiene Copolymers", Macromolecules, 32, 3727-3734 (1999).
Nojiri, A. et al., "Molecular Weight Dependence of the Glass Transition Temperature in Poly(vinyl acetate)," Japan J. Appl. Phys. 10 (1971), p. 803.
Pigeon, R. et al., Chimie Macromoleculaire Appliquee, No. 600, 40/41 (1074), pp. 139-158.
Porter, "Chapter 7: Non Ionics," Handbook of Surfactants, 1991, pp. 116-178, Chapman and Hall, New York.
Prince, L.M. ed., Macroemulsions Theory and Practice, Academic Press (1977), pp. 21-32.
Rangarajan P., et al., "Morphology of Semi-Crystalline Block Copolymers of Ethylene-(ethylene-alt-propylene)," Macromolecules, 26, 4640-4645 (1993).
Related U.S. Appl. No. 11/089,172, filed Mar. 25, 2005, Inventors: Katarina Benabdillah et al.
Richter, P. et al., "Polymer Aggregates with Crystalline Cores: The System Poly(ethylene)-poly(ethylene-propylene)," Macromolecules, 30, 1053-1068 (1997).
Specific Gravity and Viscosity of Liquid Table; available at http://www.csgnetwork.com/sgvisc.html. Sesame seed oil information originally published Mar. 28, 2002.
Thermal_Transisitons_of_Homopolymers.pdf. Thermal Transistions of Homopolymers: Glass Transistion & Melting Point Data, Accessed online Dec. 19, 2008 at: http://www.sigmaaldrich.com/etc/medialib/docs/Aldrich/General_lnformation/thermal_transitions_of_homopolymers.Par.0001.File.tmp/thermal_transitions_of_homopolymers.pdf.
Toniu, P. et al., "Process for Preparation of Block Polymers, Products Obtained by Means of the Process and Cosmetic Compositions Containing Them", 1973, French Patent Office, pp. 1-26 (English translation of French Patent No. FR2140977).
Office Action mailed Apr. 28, 2010, in co-pending U.S. Appl. No. 10/528,835.
Office Action mailed Aug. 12, 2005, in co-pending U.S. Appl. No. 10/670,478.
Office Action mailed Aug. 12, 2009 in co-pending U.S. Appl. No, 10/949,448.
Office Action mailed Aug. 18, 2009 in co-pending U.S. Appl. No. 10/529,264.
Office Action mailed Dec. 10, 2008, in co-pending U.S. Appl. No. 10/528,698.
Office Action mailed Dec. 23, 2008, in co-pending U.S. Appl. No. 10/529,266.
Office Action mailed Dec. 29, 2009 in co-pending U.S. Appl. No. 10/529,265.
Office Action mailed Dec. 3, 2009 in co-pending U.S. Appl. No. 10/528,698.
Office Action mailed Feb. 2, 2010, in co-pending U.S. Appl. No. 10/949,448.
Office Action mailed Jan. 28, 2010, in co-pending U.S. Appl. No. 10/529,264.
Office Action mailed Jan. 7, 2008, in co-pending U.S. Appl. No. 10/670,388.
Office Action mailed Jul. 21, 2009, in co-pending U.S. Appl. No. 11/878,067.
Office Action mailed Jun. 12, 2009 in co-pending U.S. Appl. No. 11/086,906.
Office Action mailed Jun. 24, 2009 in co-pending U.S. Appl. No. 10/528,698.

(56) References Cited

OTHER PUBLICATIONS

Office Action mailed Jun. 24, 2009 in co-pending U.S. Appl. No. 10/529,267.
Office Action mailed Jun. 29, 2009 in co-pending U.S. Appl. No. 10/529,266.
Office Action mailed Jun. 4, 2009 in co-pending U.S. Appl. No. 10/670,478.
Office Action mailed Jun. 8, 2009 in co-pending U.S. Appl. No. 11/089,210.
Office Action mailed Mar. 12, 2009, in co-pending U.S. Appl. No. 10/529,218.
Office Action mailed Mar. 17, 2010, in co-pending U.S. Appl. No. 10/529,318.
Office Action mailed Mar. 18, 2009, in co-pending U.S. Appl. No. 10/528,699.
Office Action mailed Mar. 18, 2009, in co-pending U.S. Appl. No. 10/573,579.
Office Action mailed Mar. 18, 2009, in related U.S. Appl. No. 11/089,172.
Office Action mailed Mar. 26, 2008, in co-pending U.S. Appl. No. 10/670,478.
Office Action mailed Mar. 30, 2010, in co-pending U.S. Appl. No. 11/089,210.
Office Action mailed Mar. 30, 2010, in co-pending U.S. Appl. No. 11/878,067.
Office Action mailed Mar. 7, 2006, in co-pending U.S. Appl. No. 10/670,478.
Office Action mailed May 3, 2007, in co-pending U.S. Appl. No. 10/670,478.
Office Action mailed Nov. 15, 2006, in co-pending U.S. Appl. No. 10/670,478.
Office Action mailed Nov. 17, 2009 in co-pending U.S. Appl. No. 10/528,835.
Office Action mailed Nov. 25, 2008, in co-pending U.S. Appl. No. 10/949,448.
Office Action mailed Nov. 25, 2008, in co-pending U.S. Appl. No. 10/670,388.
Office Action mailed Nov. 6, 2009 in co-pending U.S. Appl. No. 10/949,435.
Office Action mailed Oct. 1, 2008, in co-pending U.S. Appl. No. 10/529,318.
Office Action mailed Oct. 21, 2008, in co-pending U.S. Appl. No. 10/670,478.
Office Action mailed Oct. 27, 2009 in co-pending U.S. Appl. No. 10/529,218.
Office Action mailed Sep. 2, 2009 in co-pending U.S. Appl. No. 10/529,318.
Office Action mailed Sep. 28, 2009 in co-pending U.S. Appl. No. 10/670,478.
Office Action mailed Sep. 7, 2007, in co-pending U.S. Appl. No. 10/670,478.

* cited by examiner

BLOCK POLYMERS AND THEIR PROCESS OF PREPARATION

This application claims benefit of U.S. Provisional Application No. 60/835,907, filed Aug. 7, 2006, the contents of which are incorporated herein by reference. This application also claims benefit of priority under 35 U.S.C. §119 to French Patent Application No. FR 06 53144, filed Jul. 27, 2006, the contents of which are also incorporated herein by reference.

Disclosed herein are novel block polymers comprising at least one first block and at least one second block, wherein, in at least one embodiment, one of the blocks has a glass transition temperature of greater than 20° C. ("rigid" block) and the other block has a glass transition temperature of less than or equal to 20° C. ("flexible" block).

Polymers of similar structure are described in European Patent Application No. 1 411 069. It would be desirable, however, for such block polymers to have improved properties so as to be able to obtain therefrom cosmetic compositions having improved hold at equivalent gloss.

Thus, disclosed herein is a block polymer comprising at least one first block and at least one second block, wherein the at least one first block comprises at least one acrylate monomer of formula $CH_2=CH-COOR_2$ in which $R_2$ is a $C_4$ to $C_{12}$ cycloalkyl group and at least one methacrylate monomer of formula $CH_2=C(CH_3)-COOR'_2$ in which $R'_2$ is a $C_4$ to $C_{12}$ cycloalkyl group, and wherein the second block comprises an acrylic acid monomer and at least one monomer with a glass transition temperature of less than or equal to 20° C.

European Patent Application No. 1 411 069 describes the possibility of preparing block polymers from an acrylate monomer or from a methacrylate monomer. This document also generally describes the possibility of incorporating acrylic acid monomers. However, this document does not describe the combination of presently claimed characteristics, namely the mixture of an acrylate monomer and of a methacrylate monomer of the same alcohol in the rigid block and the presence of acrylic acid in the flexible block.

In addition, EP 1 411 069 would not prompt a person skilled in the art to modify the nature of the monomers in order to obtain a copolymer which makes it possible to improve the hold properties of a glossy cosmetic composition. Indeed, the polymers described in this document have to be combined in order to obtain a cosmetic composition simultaneously possessing these two properties.

Thus, disclosed herein is a novel block polymer. Further disclosed herein is a cosmetic composition comprising such a polymer.

Also disclosed herein is a cosmetic process for making up and/or caring for keratinous substances, comprising application, to the keratinous substances, of a cosmetic composition according to the present disclosure.

Still further disclosed herein is a process for the preparation of the block polymer and a polymer capable of being obtained by this process.

Also disclosed herein is the use of the polymer according to the present disclosure in a cosmetic composition as an agent for improving the hold of the composition while maintaining its gloss.

Finally, disclosed herein is the use of the polymer according to the present disclosure in a composition exhibiting improved hold properties and good gloss.

Block Polymers

The block polymer according to the present disclosure comprises at least one first block and at least one second block.

As used herein, the term "at least" one block is understood to mean one or more blocks.

As used herein, the term "block" polymer is understood to mean a polymer comprising at least 2 distinct blocks, for example, at least 3 distinct blocks.

According to one embodiment, the at least one first block and the at least one second block of the polymer of the present disclosure may be incompatible with one another.

As used herein, the term "blocks incompatible with one another" is understood to mean that the blend formed by a polymer corresponding to the first block and by a polymer corresponding to the second block is immiscible in the polymerization solvent, predominant by weight, of the block polymer, at ambient temperature (25° C.) and atmospheric pressure ($10^5$ Pa), for an amount of the blend of the polymers of greater than or equal to 5% by weight, with respect to the total weight of the mixture of the polymers and of the polymerization solvent, it being understood that:

i) the polymers are present in the blend in an amount such that the respective ratio by weight ranges from 10/90 to 90/10, and that ii) each of the polymers corresponding to the first and second blocks has a (weight- or number-)average molecular weight equal to that of the block polymer +/−15%.

In the case of a mixture of polymerization solvents, assuming two or more solvents present in identical proportions by weight, the blend of polymers is immiscible in at least one of them.

In the case of a polymerization carried out in a single solvent, the latter is the predominant solvent.

The block polymer according to the present disclosure comprises at least one first block and at least one second block.

According to one embodiment, the at least one first block and the at least one second block may be connected to one another via at least one intermediate segment comprising at least one constituent monomer of the first block and at least one constituent monomer of the second block.

The intermediate segment is a block comprising at least one constituent monomer of the first block and at least one constituent monomer of the second block of the polymer which makes it possible to "compatibilize" these blocks.

According to at least one embodiment, the intermediate segment comprising at least one constituent monomer of the first block and at least one constituent monomer of the second block of the polymer is a random polymer.

In another embodiment, the intermediate block essentially comprises constituent monomers of the first block and of the second block.

As used herein, the term "essentially" is understood to mean at least 85%, for example, at least 90%, at least 95%, or even 100%.

According to one embodiment, the intermediate block has a glass transition temperature Tg between the glass transition temperatures of the first and second blocks.

The block polymer according to the present disclosure may be, in at least one embodiment, a film-forming block ethylenic polymer.

As used herein, the term "ethylenic" polymer is understood to mean a polymer obtained by polymerization of monomers comprising an ethylenic unsaturation.

As used herein, the term "film-forming" polymer is understood to mean a polymer capable of forming, by itself alone or in the presence of an additional agent which is able to form a film, a continuous film which adheres to a support, for example, to keratinous substances.

In at least one embodiment, the polymer according to the present disclosure does not comprise silicon atoms in its backbone. As used herein, the term "backbone" is understood to mean the main chain of the polymer, in contrast to the pendant side chains.

In another embodiment, the polymer according to the present disclosure is water-insoluble, i.e., the polymer is insoluble in water or in a mixture of water and of linear or branched lower monoalcohols comprising from 2 to 5 carbon atoms, such as ethanol, isopropanol, and n-propanol, without modification of pH, at an active substance content of at least 1% by weight, at ambient temperature (25° C.).

According to a further embodiment, the polymer according to the present disclosure is not an elastomer.

As used herein, the term "nonelastomeric polymer" is understood to mean a polymer which, when subjected to a stress targeted at drawing it (for example, by 30% relative to its initial length), does not return to a length essentially identical to its initial length when the stress ceases.

For example, a "nonelastomeric polymer" may have an instantaneous recovery $R_i$<50% and a delayed recovery $R_{2h}$<70% after having undergone an elongation of 30%. In at least one embodiment, $R_i$ is <30% and $R_{2h}$<50%.

The nonelastomeric nature of the polymer may be determined according to the following protocol:

A polymer film is prepared by casting a solution of the polymer in a Teflon-treated matrix and then dried for 7 days in surroundings controlled at 23±5° C. and 50±10% relative humidity.

A film with a thickness of approximately 100 μm is then obtained, from which the rectangular test specimens with a width of 15 mm and a length of 80 mm are cut (for example with a hollow punch).

A tensile stress is applied to the sample using a device sold under the Zwick reference, under the same temperature and humidity conditions as for the drying.

The test specimens are drawn at a rate of 50 mm/min and the distance between the clamping jaws is 50 mm, which corresponds to the initial length ($I_0$) of the test specimen.

The instantaneous recovery Ri is determined as follows:
the test specimen is drawn by 30% ($\epsilon_{max}$), i.e., approximately 0.3 times its initial length ($I_0$),
the stress is released by applying a return rate equal to the tensioning rate, i.e., 50 mm/min, and the residual elongation of the test specimen is measured as a percentage, after returning to zero loading stress ($\epsilon_i$).

The instantaneous recovery in % ($R_i$) is given by the formula below:

$$R_i=((\epsilon_{max}-\epsilon_i)/\epsilon_{max})\times 100$$

To determine the delayed recovery, the residual elongation of the test specimen is measured as a percentage ($\epsilon_{2h}$), 2 hours after returning to the zero loading stress.

The delayed recovery in % ($R_{2h}$) is given by the formula below:

$$R_{2h}=((\epsilon_{max}-\epsilon_{2h})/\epsilon_{max})\times 100$$

According to at least one embodiment, a polymer according to the present disclosure may have an instantaneous recovery $R_i$ of 10% and a delayed recovery $R_{2h}$ of 30%.

In another embodiment, the polydispersity index of the polymer of the present disclosure may be greater than 2.

The polydispersity index I of the polymer is equal to the ratio of the weight-average mass Mw to the number-average mass Mn.

The weight-average molar masses (Mw) and the number-average molar masses (Mn) may be determined by gel permeation liquid chromatography (solvent THF, calibration curve drawn up with linear polystyrene standards, refractometric detector).

According to one embodiment, the weight-average mass (Mw) of the polymer according to the present disclosure may be less than or equal to 300 000; for example, ranging from 35 000 to 200 000, or from 45 000 to 150 000 g/mol.

In another embodiment, the number-average mass (Mn) of the polymer according to the present disclosure may be less than or equal to 70 000; for example, ranging from 10 000 to 60 000 or from 12 000 to 50 000 g/mol.

According to a further embodiment, the polydispersity index of the polymer according to the present disclosure is greater than 2, for example, ranging from 2 to 9, greater than or equal to 2.5, for example, ranging from 2.5 to 8, or greater than or equal to 2.8, for example, ranging from 2.8 to 6.

The block polymer of the present disclosure comprises at least one first block and at least one second block.

According to one embodiment, the at least one first block comprises at least one acrylate monomer of formula $CH_2=CH-COOR_2$ and at least one methacrylate monomer of formula $CH_2=C(CH_3)-COOR_2$ wherein $R_2$ is chosen from $C_4$ to $C_{12}$ cycloalkyl groups. In another embodiment, the monomers and their proportions are chosen so that the glass transition temperature of the first block is greater than 20° C.

According to a further embodiment, the second block comprises at least one acrylic acid monomer and at least one monomer with a glass transition temperature of less than or equal to 20° C. In still a further embodiment, the monomers and their proportions are chosen so that the glass transition temperature of the second block is less than or equal to 20° C.

The glass transition temperatures indicated for the first and second blocks can be theoretical Tg values determined from the theoretical Tg values of the constituent monomers of each of the blocks, which can be found in a reference handbook, such as the Polymer Handbook, $3^{rd}$ ed., 1989, John Wiley, according to the following relationship, referred to as the Fox Law:

$$1/Tg=\Sigma(\overline{\omega}_i/Tg_i),$$

wherein $\overline{\omega}_i$ is the mass fraction of the monomer i in the block under consideration and $Tg_i$ is the glass transition temperature of the homopolymer of the monomer i.

Unless otherwise indicated, the Tg values indicated for the first and second blocks in the present disclosure are theoretical Tg values.

According to one embodiment, the difference between the glass transition temperatures of the first and second blocks may be greater than 10° C., for instance, greater than 20° C., or greater than 30° C.

As used herein, the expression:
<<of between . . . and . . . >> is intended to denote a range of values, the limits of which mentioned are excluded, and the expressions
<<from . . . to . . . >> and <<ranging from . . . to . . . >> are intended to denote a range of values, the limits of which are included.

First Block

In at least one embodiment, the first block has a Tg of greater than 20° C., for example, a Tg ranging from 20 to 170° C., or greater than or equal to 50° C., for example, ranging, from 50° C. to 160° C., or from 90° C. to 130° C.

According to one embodiment, the first block comprises at least one acrylate monomer of formula $CH_2=CH-COOR_2$ wherein $R_2$ is chosen from $C_4$ to $C_{12}$ cycloalkyl groups and at least one methacrylate monomer of formula $CH_2=C(CH_3)—COOR'_2$ wherein $R'_2$ is chosen from $C_4$ to $C_{12}$ cycloalkyl groups.

In another embodiment, the first block essentially comprises the acrylate monomer and the methacrylate monomer.

The acrylate monomer and the methacrylate monomer may be present in the first block in proportions by weight of 30:70 to 70:30, for instance, 40:50 to 50:40, or equal to 50:50.

The at least one first block may be present in the block polymer in an amount ranging from 20 to 90% by weight relative to the total weight of the block polymer, for example, from 30 to 80%, or from 60 to 80%.

According to one embodiment, the first block is obtained by a polymerization of isobornyl methacrylate and of isobornyl acrylate.

In another embodiment, the first block may additionally comprise:
(meth)acrylic acid, e.g., acrylic acid,
tert-butyl acrylate,
methacrylates of formula $CH_2=C(CH_3)—COOR_1$
wherein $R_1$ is chosen from linear or branched unsubstituted alkyl groups comprising from 1 to 4 carbon atoms, such as methyl, ethyl, propyl, and isobutyl groups,
(meth)acrylamides of formula:

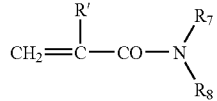

wherein $R_7$ and $R_8$, which may be identical or different, are chosen from hydrogen and linear or branched $C_1$ to $C_{12}$ alkyl groups, such as n-butyl, t-butyl, isopropyl, isohexyl, isooctyl, and isononyl groups; for instance, in at least one embodiment, $R_7$ is H and $R_8$ is a 1,1-dimethyl-3-oxobutyl group; and R' is chosen from H and methyl. Non-limiting examples of such monomers include N-butylacrylamide, N-(t-butyl)acrylamide, N-isopropylacrylamide, N,N-dimethylacrylamide, and N,N-dibutylacrylamide,
and mixtures thereof.

Second Block

In at least one embodiment, the second block has a glass transition temperature Tg of less than or equal to 20° C., for example, a Tg ranging from −100 to 20° C., less than or equal to 15° C., for example, ranging from −80° C. to 15° C., or less than or equal to 10° C., for example, ranging from −100° C. to 10° C., or from −30° C. to 10° C.

According to another embodiment, the second block comprises at least one acrylic acid monomer and at least one monomer having a Tg of less than or equal to 20° C.

The monomer having a Tg of less than or equal to 20° C. may be chosen, for example, from:
acrylates of formula $CH_2=CHCOOR_3$,
wherein $R_3$ is chosen from linear or branched unsubstituted $C_1$ to $C_{12}$ alkyl groups, with the exception of the tert-butyl group, said alkyl groups being optionally interrupted by at least one heteroatom chosen from O, N, and S;
methacrylates of formula $CH_2=C(CH_3)—COOR_4$,
wherein $R_4$ is chosen from linear or branched unsubstituted $C_6$ to $C_{12}$ alkyl groups optionally interrupted by at least one heteroatom chosen from O, N, and S;
vinyl esters of formula $R_5—CO—O—CH=CH_2$,
wherein $R_5$ is chosen from linear or branched $C_4$ to $C_{12}$ alkyl groups;
esters of vinyl alcohol and of $C_4$ to $C_{12}$ alcohols;
N—($C_4$ to $C_{12}$ alkyl)acrylamides, such as N-octylacrylamide;
and mixtures thereof.

According to one embodiment, the at least one monomer having a Tg of less than or equal to 20° C. may be chosen from isobutyl acrylate, 2-ethylhexyl acrylate, and mixtures thereof in all proportions.

In at least one embodiment, each of the first and second blocks can comprise a minor proportion of at least one constituent monomer of the other block. Thus, the first block may comprise at least one constituent monomer of the second block, and vice versa.

According to another embodiment, each of the first and/or second blocks may comprise, in addition to the monomers indicated above, at least one other monomer, referred to as additional monomers, different from the main monomers mentioned above.

The nature and the amount of the at least one additional monomer may be chosen so that the block in which they occur has the desired glass transition temperature.

The at least one additional monomer may be chosen, for example, from:
monomers comprising at least one ethylenic unsaturation comprising at least one tertiary amine functional group, such as 2-vinylpyridine, 4-vinylpyridine, dimethylaminoethyl methacrylate, diethylaminoethyl methacrylate, dimethylaminopropylmethacrylamide, and the salts thereof,
methacrylates of formula $CH_2=C(CH_3)—COOR_6$,
wherein $R_6$ is chosen from linear or branched alkyl groups comprising from 1 to 4 carbon atoms, such as methyl, ethyl, propyl, and isobutyl groups, wherein the alkyl groups are substituted by at least one substituent chosen from hydroxyl groups (such as 2-hydroxypropyl methacrylate and 2-hydroxyethyl methacrylate) and halogen atoms (such as Cl, Br, I, and F), such as trifluoroethyl methacrylate,
methacrylates of formula $CH_2=C(CH_3)—COOR_9$,
wherein $R_9$ is chosen from linear or branched $C_6$ to $C_{12}$ alkyl groups optionally interrupted by at least one heteroatom chosen from O, N, and S, wherein the alkyl groups are substituted by at least one substituent chosen from hydroxyl groups and halogen atoms (such as Cl, Br, I, and F); and
acrylates of formula $CH_2=CHCOOR_{10}$,
wherein $R_{10}$ is chosen from linear or branched $C_1$ to $C_{12}$ alkyl groups substituted by at least one substituent chosen from hydroxyl groups and halogen atoms (such as Cl, Br, I, and F), such as 2-hydroxypropyl acrylate and 2-hydroxyethyl acrylate, or $R_{10}$ is chosen from ($C_1$ to $C_{12}$ alkyl)-O-POEs (polyoxyethylenes) with repetition of the oxyethylene unit from 5 to 30 times, for example, methoxy-POE, or $R_{10}$ is chosen from polyoxyethylene groups comprising from 5 to 30 ethylene oxide units.

The at least one additional monomer may be present in the polymer in an amount ranging from 0.5 to 30% by weight, relative to the total weight of the polymer. According to one embodiment, the polymer of the present disclosure does not comprise an additional monomer.

In at least one embodiment, the polymer of the disclosure comprises at least isobornyl acrylate and isobornyl methacrylate monomers in the first block and isobutyl acrylate and acrylic acid monomers in the second block.

According to another embodiment, the polymer comprises at least isobornyl acrylate and isobornyl methacrylate monomers in an equivalent proportion by weight in the first block and isobutyl acrylate and acrylic acid monomers in the second block.

In a further embodiment, the polymer comprises at least isobornyl acrylate and isobornyl methacrylate monomers in an equivalent proportion by weight in the first block and isobutyl acrylate and acrylic acid monomers in the second block, wherein the first block is present in an amount of 70% by weight relative to the total weight of the polymer.

In still a further embodiment, the polymer comprises at least isobornyl acrylate and isobornyl methacrylate monomers in an equivalent proportion by weight in the first block and isobutyl acrylate and acrylic acid monomers in the second block, wherein the first block with a Tg of greater than 20° C. is present in an amount of 70% by weight relative to the total weight of the polymer and acrylic acid is present in an amount of 5% by weight relative to the total weight of the polymer.

According to one embodiment, the polymer comprises from 1 to 10% by weight, for example, from 3 to 8% by weight, of acrylic acid monomer.

According to another embodiment, the second block comprises at least one acrylic acid monomer and at least one acrylate monomer of formula $CH_2=CHCOOR_3$, wherein $R_3$ is chosen from linear or branched unsubstituted $C_1$ to $C_{12}$ alkyl groups, with the exception of the tert-butyl group, said alkyl groups being optionally interrupted by at least one heteroatom chosen from O, N, and S. In this embodiment, the acrylic acid monomer and the acrylate monomer may be present in the second block in proportions by weight ranging from 10:90 to 20:80, for example, 30:70.

Processes

Also disclosed herein is a process for the preparation of a polymer comprising mixing, in the same reactor, at least one polymerization solvent, at least one initiator, at least one acrylic acid monomer, at least one monomer with a glass transition temperature of less than or equal to 20° C., at least one acrylate monomer of formula $CH_2=CH-COOR_2$ wherein $R_2$ is chosen from $C_4$ to $C_{12}$ cycloalkyl groups, and at least one methacrylate monomer of formula $CH_2=C(CH_3)-COOR'_2$ wherein $R'_2$ is chosen from $C_4$ to $C_{12}$ cycloalkyl groups, according to the following sequence comprising:

adding to the reactor a portion of the at least one polymerization solvent and a portion of the at least one initiator, and heating the resulting mixture to a reaction temperature ranging from 60 to 120° C., subsequently adding to the reactor the at least one acrylate monomer of formula $CH_2=CH-COOR_2$ and the at least one methacrylate monomer of formula $CH_2=C(CH_3)-COOR'_2$, in a first fluid addition, and leaving the resulting mixture to react for a time T corresponding to a degree of conversion of the monomers of at most 90%, subsequently adding to the reactor, in a second fluid addition, additional polymerization initiator, the at least one acrylic acid monomer, and the at least one monomer with a glass transition temperature of less than or equal to 20° C. and leaving the resulting mixture to react for a time T' at the end of which the degree of conversion of the said monomers reaches a plateau, and bringing the reaction mixture back to ambient temperature.

As used herein, the term <<polymerization solvent>> is understood to mean a solvent or a mixture of solvents. The polymerization solvent may be chosen, for example, from ethyl acetate, butyl acetate, alcohols, such as isopropanol and ethanol, aliphatic alkanes, such as isododecane, and mixtures thereof. In at least one embodiment, the polymerization solvent is chosen from mixtures of butyl acetate and isopropanol and mixtures of butyl acetate and isododecane.

According to one embodiment, the ratio by weight of the at least one polymerization solvent to the polymer obtained may range from 40 to 60% at the end of the reaction. In another embodiment, the at least one polymerization initiator can be a peroxide.

According to at least one embodiment, an additional amount of the at least one polymerization solvent can be added to the reactor during the second fluid addition, in addition to the polymerization solvent added in the first fluid addition.

Further disclosed herein is a process for the preparation of a polymer comprising mixing, in the same reactor, at least one polymerization solvent, at least one initiator, at least one acrylic acid monomer, at least one monomer with a glass transition temperature of less than or equal to 20° C., at least one acrylate monomer of formula $CH_2=CH-COOR_2$ wherein $R_2$ is chosen from $C_4$ to $C_{12}$ cycloalkyl groups and at least one methacrylate monomer of formula $CH_2=C(CH_3)-COOR'_2$ wherein $R'_2$ is chosen from $C_4$ to $C_{12}$ cycloalkyl groups, according to the following sequence comprising:

adding to the reactor a portion of the at least one polymerization solvent and a portion of the at least one initiator, and heating the resulting mixture to a reaction temperature ranging from 60 to 120° C., subsequently adding to the reactor, in a first fluid addition, the at least one acrylic acid monomer and the at least one monomer with a glass transition temperature of less than or equal to 20° C., and leaving the resulting mixture to react for a time T corresponding to a degree of conversion of the monomers of at most 90%, subsequently adding to the reactor, in a second fluid addition, additional polymerization initiator, the at least one acrylate monomer of formula $CH_2=CH-COOR_2$ and the at least one methacrylate monomer of formula $CH_2=C(CH_3)-COOR'_2$, and leaving the resulting mixture to react for a time T' at the end of which the degree of conversion of the said monomers reaches a plateau, and bringing the reaction mixture back to ambient temperature.

In at least one embodiment, the polymerization temperature is 90° C.

In another embodiment, the reaction time after the second fluid addition may range from 3 to 6 hours.

The monomers employed in the context of this process and their proportions can be chosen from those described above.

In at least one embodiment, the at least one acrylic acid may be present in the reactor in an amount ranging from 1 to 10% by weight, for example, from 3 to 8% by weight, relative to the weight of all the monomers introduced into the reactor. Furthermore, in another embodiment, the at least one acrylic acid monomer and the at least one monomer with a glass transition temperature of less than or equal to 20° C. may be present in the reactor in proportions by weight ranging from 10:90 to 20:80, for instance, 30:70.

Also disclosed herein is a polymer capable of being obtained by the processes described above.

Cosmetic Compositions

Further disclosed herein are cosmetic compositions comprising at least one polymer of the present disclosure. Generally, these compositions may comprise from 0.1 to 60% by weight of active material (or dry matter) of at least one polymer according to the present disclosure, for example, from 0.5 to 50% by weight, or from 1 to 40% by weight.

The cosmetic compositions according to the present disclosure comprise, in addition to the at least one polymer, at least one physiologically acceptable medium, i.e., a medium compatible with keratinous substances, such as the skin, hair, eyelashes, eyebrows, and nails.

According to at least one embodiment, the at least one physiologically acceptable medium may comprise at least one appropriate physiologically acceptable solvent.

The composition may thus comprise a hydrophilic medium chosen from water and mixtures of water and at least one hydrophilic organic solvent, such as alcohols, for example, linear or branched lower monoalcohols comprising from 2 to 5 carbon atoms, such as ethanol, isopropanol, and n-propanol; polyols, such as glycerol, diglycerol, propylene glycol, sorbitol, pentylene glycol, and polyethylene glycols; hydrophilic $C_2$ ethers; and hydrophilic $C_2$-$C_4$ aldehydes.

The at least one physiologically acceptable medium may be present in the composition according to the present disclosure in an amount ranging from 0.1% to 99% by weight, relative to the total weight of the composition, for example, from 10% to 80% by weight.

The composition may comprise, in addition to the block polymer of the present disclosure, at least one additional polymer, such as a film-forming polymer. As used herein, the term "film-forming polymer" is understood to mean a polymer capable of forming, by itself alone or in the presence of an additional agent which is able to form a film, a continuous film which adheres to a support, for example, keratinous substances.

Non-limiting examples of suitable film-forming polymers include synthetic polymers of radical type or of polycondensate type, polymers of natural origin, and blends thereof. In at least one embodiment, the at least one film-forming polymer may be chosen from acrylic polymers, polyurethanes, polyesters, polyamides, polyureas, and cellulose polymers, such as nitrocellulose.

The composition may also comprise a fatty phase comprising at least one fatty substance which is liquid at ambient temperature (generally 25° C.) and/or at least one fatty substance which is solid at ambient temperature, such as waxes, pasty fatty substances, gums, and their mixtures. These fatty substances can be of animal, vegetable, mineral, or synthetic origin. This fatty phase may additionally comprise lipophilic organic solvents.

Examples of fatty substances which are liquid at ambient temperature, often referred to as oils, include, but are not limited to, hydrocarbon oils of animal origin, such as perhydrosqualene; vegetable hydrocarbon oils, such as liquid triglycerides of fatty acids with 4 to 10 carbon atoms, such as triglycerides of heptanoic or octanoic acids, sunflower, maize, soybean, grape seed, sesame, apricot, macadamia, castor, and avocado oils, triglycerides of caprylic/capric acids, jojoba oil, and shea butter; linear or branched hydrocarbons of mineral or synthetic origin, such as liquid paraffins and their derivatives, liquid petrolatum, polydecanes, and hydrogenated polyisobutene, such as parleam; synthetic esters and ethers, for instance, of fatty acids, such as, Purcellin oil, isopropyl myristate, 2-ethylhexyl palmitate, 2-octyldodecyl stearate, 2-octyidodecyl erucate, and isostearyl isostearate; hydroxylated esters, such as isostearyl lactate, octyl hydroxystearate, octyldodecyl hydroxystearate, diisostearyl malate, triisocetyl citrate, and heptanoates, octanoates, or decanoates of fatty alcohols; polyol esters, such as propylene glycol dioctanoate, neopentyl glycol diheptanoates, diethylene glycol diisononanoate, and pentaerythritol esters; fatty alcohols comprising from 12 to 26 carbon atoms, such as octyldodecanol, 2-butyloctanol, 2-hexyldecanol, 2-undecylpentadecanol, and oleyl alcohol; partially hydrocarbon-comprising and/or silicone-comprising fluorinated oils; silicone oils, such as volatile or nonvolatile and linear or cyclic polymethylsiloxanes (PDMSs) which are liquid or pasty at ambient temperature, such as cyclomethicones, dimethicones, optionally comprising a phenyl group, such as phenyl trimethicones, phenyltrimethylsiloxydiphenylsiloxanes, diphenylmethyldimethyltrisiloxanes, diphenyl dimethicones, phenyl dimethicones, and polymethylphenylsiloxanes; and mixtures thereof.

The at least one fatty substance which is liquid at ambient temperature may be present in the composition in an amount ranging from 0.01 to 90% by weight, for example, from 0.1 to 85% by weight, relative to the total weight of the composition.

As used herein, the term "pasty fatty substance" is understood to mean a viscous product comprising a liquid fraction and a solid fraction, for instance, fatty substances having a melting point ranging from 20 to 55° C., preferably 25 to 45° C., and/or a viscosity at 40° C. ranging from 0.1 to 40 Pa·s (1 to 400 poises), such as from 0.5 to 25 Pa·s, measured with a Contraves TV or Rhéomat 80. A person skilled in the art can choose, from the MS-r3 and MS-r4 spindles, on the basis of his or her general knowledge, a spindle which makes it possible to measure the viscosity, so as to be able to carry out the measurement of the viscosity of the pasty compound tested.

The melting point values correspond, according to the present disclosure, to the melting peak measured by the differential scanning calorimetry method with a rise in temperature of 5 or 10° C./min.

The composition of the present disclosure may comprise at least one pasty fatty substance. These fatty substances may be chosen, for example, from hydrocarbon compounds (comprising carbon and hydrogen atoms and optionally ester groups), optionally of polymer type; silicone and/or fluorinated compounds; and mixtures of hydrocarbon and/or silicone and/or fluorinated compounds. In the case of a mixture of different pasty fatty substances, in at least one embodiment, pasty hydrocarbon compounds may be used.

Non-limiting examples of pasty compounds suitable for use in the composition according to the present disclosure include lanolins and lanolin derivatives, such as acetylated lanolins, oxypropylenated lanolins, and isopropyl lanolate, having a viscosity ranging from 18 to 21 Pa·s, for example, from 19 to 20.5 Pa·s, and/or a melting point of 30 to 55° C., and mixtures thereof; esters of fatty acids or of fatty alcohols, such as those comprising from 20 to 65 carbon atoms (melting point ranging from 20 to 35° C. and/or viscosity at 40° C. ranging from 0.1 to 40 Pa·s), such as triisostearyl citrate and cetyl citrate; arachidyl propionate; poly(vinyl laurate); cholesterol esters, such as triglycerides of vegetable origin, such as hydrogenated vegetable oils, viscous polyesters, such as poly(12-hydroxystearic acid), and mixtures thereof; and triglycerides of vegetable origin, for instance, derivatives of hydrogenated castor oil, such as "Thixinr" from Rheox.

Silicone pasty fatty substances may also be used, such as polydimethylsiloxanes (PDMSs) having pendant chains of alkyl and/or alkoxy type comprising from 8 to 24 carbon atoms and a melting point of 20-55° C., such as stearyl dimethicones, for instance, those sold by Dow Corning under the trade names of DC2503 and DC25514, and mixtures thereof.

The at least one pasty fatty substance may be present in the composition in an amount ranging from 0.5 to 60% by weight, relative to the total weight of the composition, for example, from 2-45% by weight, or from 5-30% by weight.

The composition according to the present disclosure may also comprise at least one cosmetically acceptable (e.g., acceptable tolerance, acceptable toxicology, and/or acceptable feel) organic solvent.

The at least one organic solvent may be present in the composition in an amount ranging from 0 to 90% by weight, for example, from 0.1 to 90%, from 10 to 90%, or from 30 to 90% by weight, relative to the total weight of the composition.

Non-limiting examples of organic solvents which can be used in the composition of the present disclosure, in addition to the hydrophilic organic solvents mentioned above, include ketones which are liquid at ambient temperature, such as methyl ethyl ketone, methyl isobutyl ketone, diisobutyl ketone, isophorone, cyclohexanone, and acetone; propylene glycol ethers which are liquid at ambient temperature, such as propylene glycol monomethyl ether, propylene glycol monomethyl ether acetate, and dipropylene glycol mono(n-butyl)ether; short-chain esters (comprising from 3 to 8 carbon atoms in total), such as ethyl acetate, methyl acetate, propyl acetate, n-butyl acetate, and isopentyl acetate; ethers which are liquid at ambient temperature, such as diethyl ether, dimethyl ether, and dichlorodiethyl ether; alkanes which are liquid at ambient temperature, such as decane, heptane, dodecane, isododecane, and cyclohexane; cyclic aromatic compounds which are liquid at ambient temperature, such as toluene and xylene; aldehydes which are liquid at ambient temperature, such as benzaldehyde and acetaldehyde; and mixtures thereof.

As used herein, the term "wax" is understood to mean a lipophilic compound which is solid at ambient temperature (25° C.), which exhibits a reversible solid/liquid change in state, and which has a melting point of greater than or equal to 30° C. which can range up to 120° C.

On bringing the wax to the liquid state (melting), it is possible to render it miscible with oils possibly present and to form a microscopically homogeneous mixture but, on bringing the temperature back to ambient temperature, recrystallization of the wax in the oils of the mixture is obtained. The melting point of the wax can be measured using a differential scanning calorimeter (DSC), for example the calorimeter sold under the name DSC 30 by Metler.

The wax may also exhibit a hardness ranging from 0.05 MPa to 15 MPa, for example, from 6 MPa to 15 MPa. The hardness may be determined by the measurement of the compressive force, measured at 20° C. using the texture analyzer sold under the name TA-TX2i by Rheo, equipped with a stainless steel cylinder with a diameter of 2 mm which is displaced at the measurement rate of 0.1 mm/s and which penetrates into the wax to a depth of penetration of 0.3 mm.

Suitable waxes may be chosen, for example, from hydrocarbon, fluorinated, and/or silicone waxes and can be of vegetable, mineral, animal, and/or synthetic origin. In at least one embodiment, the waxes may exhibit a melting point of greater than 25° C., for example, greater than 45° C.

Examples of waxes which can be used in the composition of the present disclosure include, but are not limited to, beeswax, carnauba wax, candelilla wax, paraffin wax, microcrystalline waxes, ceresin, and ozokerite; synthetic waxes, such as polyethylene waxes or Fischer-Tropsch waxes; and silicone waxes, such as alkyl and alkoxy dimethicones comprising from 16 to 45 carbon atoms.

The gums may be chosen, for instance, from polydimethylsiloxanes (PDMSs) of high molecular weight, cellulose gums, and polysaccharides and the pasty substances may be chosen, for example, from hydrocarbon compounds, such as lanolins and their derivatives, and PDMSs.

The nature and the amount of the solid substances depend on the mechanical properties and textures desired. By way of non-limiting example, the composition may comprise from 0 to 50% by weight of waxes, relative to the total weight of the composition, such as from 1 to 30% by weight.

The polymer of the present disclosure may be used in combination with at least one additional agent which is able to form a film. Agents which are able to form a film can be chosen from any compound known to a person skilled in the art as being capable of fulfilling the desired function, such as plasticizers and coalescence agents.

The composition according to the present disclosure may further comprise at least one coloring material chosen from water-soluble dyes and pulverulent coloring materials, such as pigments, pearlescent agents, and glitter, well known to a person skilled in the art. The at least one coloring materials may be present in the composition in an amount ranging from 0.01% to 50% by weight, relative to the total weight of the composition, for example, from 0.01% to 30% by weight.

As used herein, the term "pigments" is understood as meaning white or coloured and inorganic or organic particles of any shape which are insoluble in the physiological medium and which are intended to color the composition.

As used herein, the term "pearlescent agents" should be understood as meaning iridescent particles of any shape produced, for example, by certain mollusks in their shells or else synthesized.

The pigments can be white or coloured and inorganic or organic. Non-limiting example of suitable inorganic pigments include titanium dioxide, optionally surface-treated; zirconium and cerium oxides; zinc, iron (e.g., black, yellow, and red), and chromium oxides; manganese violet; ultramarine blue; chromium hydrate; ferric blue; and metal powders, such as aluminum powder and copper powder.

Examples of organic pigments include, but are not limited to, carbon black, pigments of D & C type, and lakes, based on cochineal carmine, of barium, strontium, calcium, and aluminum.

The pigments may also be chosen from pigments with an effect, such as particles comprising an organic or inorganic and natural or synthetic substrate, for example, glass, acrylic resins, polyester, polyurethane, poly(ethylene terephthalate), ceramics, and aluminas, the substrate being optionally covered with metal substances, such as aluminum, gold, silver, platinum, copper, and bronze, and/or with metal oxides, such as titanium dioxide, iron oxide, and chromium oxide, and mixtures thereof.

The pearlescent pigments may be chosen, for instance, from white pearlescent pigments, such as mica covered with titanium oxide and/or with bismuth oxychloride, colored pearlescent pigments, such as titanium oxide-coated mica covered with iron oxides, titanium oxide-coated mica covered with, for example, ferric blue and/or chromium oxide, and titanium oxide-coated mica covered with an organic pigment described above, and pearlescent pigments based on bismuth oxychloride. Interferential pigments may also be used, for example, liquid crystal and multilayer pigments.

Suitable water-soluble dyes may include, for example, beetroot juice and methylene blue.

The composition according to the present disclosure may further comprise at least one filler, present, for example, in an amount ranging from 0.01% to 50% by weight, relative to the total weight of the composition, such as from 0.01% to 30% by weight. As used herein, the term "fillers" is understood as meaning colorless or white and inorganic or synthetic particles of any shape which are insoluble in the medium of the composition, whatever the temperature at which the composition is manufactured. These fillers may be used to modify the rheology and/or the texture of the composition.

The fillers may be chosen from inorganic and organic fillers of any shape, such as platelet, spherical, and oblong, whatever the crystallographic form (for example, leaf, cubic, hexagonal, orthorhombic, and the like). Non-limiting examples of such fillers include talc, mica, silica, kaolin, polyamide (Nylon®) powders (Orgasol® from Atochem), poly-β-alanine powders, polyethylene powders, powders formed of tetrafluoroethylene polymers (Teflon®), lauroyllysine, starch, boron nitride, polymeric hollow microspheres, such as those of polyvinylidene chloride/acrylonitrile, for example Expancel® (Nobel Industry), and of acrylic acid copolymers (Polytrap® from Dow Corning), silicone resin microbeads (Tospearls® from Toshiba, for example), polyorganosiloxane elastomer particles, precipitated calcium carbonate, magnesium carbonate, basic magnesium carbonate, hydroxyapatite, hollow silica microspheres (Silica Beads® from Maprecos), glass and ceramic microcapsules, and metal soaps derived from organic carboxylic acids comprising from 8 to 22 carbon atoms, such as from 12 to 18 carbon atoms, for example zinc stearate, magnesium stearate, lithium stearate, zinc laurate, and magnesium myristate.

The composition according to the present disclosure may further comprise at least one additional ingredient commonly used in cosmetics, such as vitamins, thickeners, trace elements, softeners, sequestering agents, fragrances, basifying and acidifying agents, preservatives, sunscreen agents, surfactants, antioxidants, agents for combating hair loss, antidandruff agents, propellants, and mixtures thereof.

It is to be understood that a person skilled in the art will take care to choose the at least one optional additional compound and/or amounts thereof so that the advantageous properties of the corresponding composition according to the present disclosure are not, or are not substantially, detrimentally affected by the envisaged addition.

The composition according to the invention can be provided in a form chosen from suspensions, dispersions, solutions, gels, emulsions, such as oil-in-water (O/W), water-in-oil (W/O), and multiple (e.g., W/O/W, polyol/O/W, and O/W/O) emulsions, creams, foams, dispersions of vesicles, such as dispersions of ionic or nonionic lipids, two-phase and multiphase lotions, powders, and pastes, such as soft pastes (e.g., pastes having a dynamic viscosity at 25° C. ranging from 0.1 to 40 Pa·s under a shear rate of 200 s$^{-1}$, after measuring for 10 minutes in cone/plate geometry). In at least one embodiment, the composition can be anhydrous; for example, it can be an anhydrous paste.

A person skilled in the art can choose the appropriate dosage form and its method of preparation on the basis of knowledge generally available in the art, taking into account, on the one hand, the nature of the constituents used, such as their solubility in the support, and, on the other hand, the application envisaged for the composition.

The composition according to the present disclosure may be chosen from makeup compositions, such as products for the complexion (foundation), face powders, eyeshadows, products for the lips, concealers, blushers, mascaras, eyeliners, products for making up the eyebrows, and lip and eye pencils; products for the nails, such as nail varnishes; products for making up the body; and products for making up the hair (e.g., hair mascaras).

The composition according to the present disclosure can also be chosen from products for caring for the skin of the body and/or face, such as antisun products and products for coloring the skin (such as self-tanning products).

The composition according to the present disclosure can also be chosen from hair products, such as products for the form retention of the hairstyle and/or the shaping of the hair. The hair compositions may be chosen, for example, from shampoos, gels, hair setting lotions, blowdrying lotions, and fixing and styling compositions.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

Example 1

Preparation of a Poly(Isobornyl Acrylate/Isobornyl Methacrylate/Isobutyl Acrylate/Acrylic Acid) Polymer 300 g of isododecane were introduced into a 1 liter reactor and then the temperature was increased so as to pass from ambient temperature (25° C.) to 90° C. in 1 hour.

105 g of isobornyl methacrylate (manufactured by Arkema), 105 g of isobornyl acrylate (manufactured by Arkema), and 1.8 g of 2,5-bis(2-ethylhexanoylperoxy)-2,5-dimethylhexane (Trigonox® 141 from Akzo Nobel) were subsequently added at 90° C. over 1 hour.

The mixture was maintained at 90° C. for 1 h 30.

75 g of isobutyl acrylate (manufactured by Fluka), 15 g of acrylic acid, and 1.2 g of 2,5-bis(2-ethylhexanoylperoxy)-2,5-dimethylhexane were subsequently introduced into the preceding mixture, still at 90° C., over 30 minutes.

The mixture was maintained at 90° C. for 3 hours and then the combined product was cooled.

A solution comprising 50% of polymer active material in isododecane was obtained.

A polymer comprising a first rigid poly(isobornyl acrylate/isobornyl methacrylate) block having a Tg of 110° C., a second flexible poly(isobutyl acrylate/acrylic acid) block having a Tg of −9° C., and an intermediate block which was a random isobornyl acrylate/isobornyl methacrylate/isobutyl acrylate/acrylic acid polymer was obtained.

Examples of Comparative Polymer, Examples of Polymer 2 and 3

The comparative example was prepared according to the teaching of Example 9 of European Patent Application No. 1 411 069: poly(isobornyl acrylate/isobornyl methacrylate/isobutyl acrylate):

100 g of isododecane were introduced into a 1 liter reactor and then the temperature was increased so as to pass from ambient temperature (25° C.) to 90° C. in 1 hour.

105 g of isobornyl acrylate, 105 g of isobornyl methacrylate, 110 g of isododecane, and 1.8 g of 2,5-bis(2-ethylhexanoylperoxy)-2,5-dimethylhexane (Trigonox® 141 from Akzo Nobel) were subsequently added at 90° C. over 1 hour.

The mixture was maintained at 90° C. for 1 h 30.

90 g of isobutyl acrylate, 90 g of isododecane, and 1.2 g of 2,5-bis(2-ethylhexanoylperoxy)-2,5-dimethylhexane were subsequently introduced into the preceding mixture, still at 90° C., over 30 minutes.

The mixture was maintained at 90° C. for 3 hours and then the combined product was cooled.

A solution comprising 50% of polymer active material in isododecane was obtained.

A polymer comprising a first poly(isobornyl acrylate/isobornyl methacrylate) block having a Tg of 128° C., a second poly(isobutyl acrylate) block having a Tg of −20° C., and an intermediate block which was a random isobornyl acrylate/isobornyl methacrylate/isobutyl acrylate polymer was obtained.

Inventive examples 2 and 3 were prepared according to the procedure described in Example 1.

| Examples | First fluid addition (% by wt.) | | Second fluid additon (% by wt.) | |
|---|---|---|---|---|
|  | Isobornyl acrylate | Isobornyl methacrylate | Isobutyl acrylate | Acrylic acid |
| Comparative | 35 | 35 | 30 | |
| Example 1 | 35 | 35 | 25 | 5 |
| Example 2 | 25 | 25 | 45 | 5 |
| Example 3 | 30 | 30 | 35 | 5 |

Hold Towards Oil of the Polymers of the Examples

This measurement is taken by placing a drop of olive oil on a dry polymer film.

A polymer film was produced from a 20% solution in isododecane. 0.5 ml was spread over a 2.5×7.5 cm glass plate and was left to dry at ambient temperature for 24 hours. Subsequently, 1 ml of olive oil was spread over the polymer film. After the desired time (1 hour or 24 hours), the excess oil was wiped from the film and the latter was weighed in order to determine its increase in weight.

The comparative polymer was tacky after 1 h; and an increase in weight of 5.5% was observed after 24 h, whereas the polymer of Example 3 was nontacky after 1 h; and its increase in weight was only 1% after 24 h.

The increase in weight and the tack reflect the sensitivity of the polymer to the olive oil. The greater the sensitivity, the more readily the deposited layer will be detrimentally affected during meals and the hold will be poorer. The hold of the polymer of Example 1 is better than that of the comparative example.

Gloss Measured with a Gloss Meter on a Dry Deposited Layer of Polymer

The gloss can be conventionally measured by the following method using a gloss meter.

A layer with a thickness of 50 μm of a 50% solution of a polymer in the synthesis solvent (isododecane) was spread using an automatic spreader over a Leneta® contrast chart with the reference Form 1A Penopac. The layer covered at least the black background of the chart. The deposited layer was left to dry for 24 hours at a temperature of 25° C. and then the 200 gloss was measured on the black background using a Dr Lange® Ref 03 gloss meter.

The 20° gloss of the polymers of Examples 1, 2, and 3 was respectively equal to 80, 74, and 75, whereas the gloss of the comparative polymer was 71.

The 60° gloss was measured as above.

The 60° gloss of the polymers of Examples 1, 2, and 3 was respectively equal to 90, 87, and 87, whereas the gloss of the comparative polymer was 86.

Example of Liquid Gloss Comprising the Polymer of Example 1

The procedure for 200 g of the following formulation is as follows:

The pigments were ground 3 times in a triple roll mill in octyldodecanol brought beforehand to 60° C. The ground material was left to cool at ambient temperature (25° C.) in a jacketed heating pan or in a beaker.

The copolymer, the squalane, the polybutylene, the pearlescent agents, and the fragrance were added to the ground material. The combined mixture was stirred using a turbine mixer (type: Rayneri) in order to homogenize.

When the mixture was homogeneous, the polyphenyltrimethylsiloxydimethylsiloxane was added with stirring at 800 revolutions/minute with the Rayneri over approximately 30 minutes.

Finally, the pyrogenic silica was added gradually and stirring with the turbine mixer was maintained at 1000 revolutions/minute for 20 minutes.

| Name | Concentration (% by weight) |
|---|---|
| Refined vegetable perhydrosqualene (INCI name = squalane) | 10.86 |
| 2-Octyldodecanol | 15.39 |
| Rutile titanium oxide treated with alumina/silica/trimethylolpropane | 2.74 |
| Red 7 | 0.54 |
| Lake Blue 1 | 0.16 |
| Lake Yellow 6 | 2.58 |
| Black iron oxide | 0.25 |
| Mica/titanium dioxide/brown iron oxide | 2 |
| Polyphenyltrimethylsiloxydimethylsiloxane [1] | 20.03 |
| Hydrophobic pyrogenic silica surface-treated with dimethylsilane [3] | 4.5 |
| Poly(isobornyl methacrylate-co-isobornyl acrylate-co-isobutyl acrylate-co-acrylic acid) at an active material content of 50% in isododecane of Example 1 | 30 |
| Polybutylene [2] | 10.65 |
| Fragrance | 0.3 |
| Total | 100 |

[1] Belsil PDM 1000 from Wacker (viscosity 1000 cPs; MW: 9000)
[2] Indopol H 100 (MW: 920)
[3] Aerosil R 972 from Degussa This gloss composition, applied to the lips in a single movement, exhibited satisfactory properties of comfort and of gloss. The hold of the composition was also improved; the composition did not migrate into the wrinkles and fine lines of the outline of the lips.

What is claimed is:

1. A block polymer comprising at least one first block, at least one second block, and an intermediate block linking the at least one first block and the at least one second block,
   wherein the first block consists essentially of at least one acrylate monomer of formula $CH_2\!=\!CH\!-\!COOR_2$ wherein $R_2$ is chosen from $C_4$ to $C_{12}$ cycloalkyl groups and at least one methacrylate monomer of formula $CH_2\!=\!C(CH_3)\!-\!COOR'_2$ wherein $R'_2$ is chosen from $C_4$ to $C_{12}$ cycloalkyl groups, and wherein the second block comprises at least one acrylic acid monomer and at least one acrylate monomer with a glass transition temperature of less than or equal to 20° C. chosen from monomers of formula $CH_2=CHCOOR_3$, wherein $R_3$ is chosen from linear or branched unsubstituted $C_1$ to $C_{12}$ alkyl groups, with the exception of the tert-butyl group, wherein the at least one acrylic acid monomer and the at least one acrylate monomer with a glass transition temperature of less than or equal to 20° C. chosen from monomers of formula $CH_2=CHCOOR_3$ are present in the block polymer in proportions by weight ranging from 10:90 to 20:80, wherein the intermediate block comprises at least one constituent monomer of the first block and at least one constituent monomer of the second block.

2. The polymer of claim 1, wherein the polymer has a polydispersity index of greater than 2.

3. The polymer of claim 1, wherein the at least one acrylate monomer of formula $CH_2=CH-COOR_2$ and the at least one methacrylate monomer of formula $CH_2=C(CH_3)-COOR'_2$ are present in the polymer in proportions by weight ranging from 30:70 to 70:30.

4. The polymer of claim 3, wherein the at least one acrylate monomer of formula $CH_2=CH-COOR_2$ and the at least one methacrylate monomer of formula $CH_2=C(CH_3)-COOR'_2$ are present in the polymer in proportions by weight ranging from 40:50 and 50:40.

5. The polymer of claim 1, wherein $R_2$ and $R'_2$ are isobornyl radicals.

6. The polymer of claim 1, wherein the at least one first block is present in the polymer in an amount ranging from 20 to 90% by weight relative to the total weight of the polymer.

7. The polymer of claim 6, wherein the at least one first block is present in the polymer in an amount ranging from 60 to 80% by weight relative to the total weight of the polymer.

8. The polymer of claim 1, wherein the at least one acrylic acid monomer is present in the polymer in an amount ranging from 1 to 10% by weight relative to the total weight of the polymer.

9. The polymer of claim 8, wherein the at least one acrylic acid monomer is present in the polymer in an amount ranging from 3 to 8% by weight relative to the total weight of the polymer.

10. The polymer of claim 1, wherein the at least one acrylate monomer of formula $CH_2=CHCOOR_3$ is isobutyl acrylate.

11. The polymer of claim 1, wherein the at least one second block comprises at least one acrylic acid monomer and at least one isobutyl acrylate monomer and the first block comprises at least one isobornyl acrylate monomer and at least one isobornyl methacrylate monomer.

12. A cosmetic composition comprising at least one block polymer, wherein the block polymer comprises:

at least one first block, at least one second block, and an intermediate block linking the at least one first block and the at least one second block, wherein the first block consists essentially of at least one acrylate monomer of formula $CH_2=CH-COOR_2$ wherein $R_2$ is chosen from $C_4$ to $C_{12}$ cycloalkyl groups and at least one methacrylate monomer of formula $CH_2=C(CH_3)-COOR'_2$ wherein $R'_2$ is chosen from $C_4$ to C12 cycloalkyl groups, and the second block comprises at least one acrylic acid monomer and at least one acrylate monomer with a glass transition temperature of less than or equal to 20° C. chosen from acrylate monomers of formula $CH_2=CHCOOR_3$, wherein $R_3$ is chosen from linear or branched unsubstituted $C_1$ to $C_{12}$ alkyl groups, with the exception of the tert-butyl group, wherein the at least one acrylic acid monomer and the at least one acrylate monomer with a glass transition temperature of less than or equal to 20° C. chosen from monomers of formula $CH_2=CHCOOR_3$ are present in the block polymer in proportions by weight ranging from 10:90 to 20:80, wherein the intermediate block comprises at least one constituent monomer of the first block and at least one constituent monomer of the second block.

13. The cosmetic composition of claim 12, wherein it is a composition for making up and/or caring for keratinous substances.

14. The cosmetic composition of claim 12, wherein it is a nail varnish.

15. The cosmetic composition of claim 12, wherein it is a product for making up the lips.

16. A cosmetic process for making up and/or caring for keratinous substances, comprising applying to the keratinous substances a cosmetic composition comprising at least one block polymer, wherein the block polymer comprises:

at least one first block, at least one second block, and an intermediate block linking the at least one first block and the at least one second block, wherein the first block consists essentially of at least one acrylate monomer of formula $CH_2=CH-COOR_2$ wherein $R_2$ is chosen from $C_4$ to $C_{12}$ cycloalkyl groups and at least one methacrylate monomer of formula $CH_2=C(CH_3)-COOR'_2$ wherein $R'_2$ is chosen from $C_4$ to $C_{12}$ cycloalkyl groups, and wherein the at least one acrylic acid monomer and the at least one acrylate monomer with a glass transition temperature of less than or equal to 20° C. chosen from monomers of formula $CH_2=CHCOOR_3$ are present in the block polymer in proportions by weight ranging from 10:90 to 20:80, wherein the intermediate block comprises at least one constituent monomer of the first block and at least one constituent monomer of the second block.

17. A process for improving the hold of a cosmetic composition while maintaining its gloss, comprising including in said cosmetic composition at least one block polymer, wherein the block polymer comprises:

at least one first block, at least one second block, and an intermediate block linking the at least one first block and the at least one second block, wherein the first block consists essentially of at least one acrylate monomer of formula $CH_2=CH-COOR_2$ wherein $R_2$ is chosen from $C_4$ to $C_{12}$ cycloalkyl groups and at least one methacrylate monomer of formula $CH_2=C(CH_3)-COOR'_2$ wherein $R'_2$ is chosen from $C_4$ to $C_{12}$ cycloalkyl groups, and the second block comprises at least one acrylic acid monomer and at least one acrylate monomer with a glass transition temperature of less than or equal to 20° C. chosen from monomers of formula $CH_2=CHCOOR_3$, wherein $R_3$ is chosen from linear or branched unsubstituted $C_1$ to $C_{12}$ alkyl groups, with the exception of the tert-butyl group, wherein the at least one acrylic acid monomer and the at least one acrylate monomer with a glass transition temperature of less than or equal to 20° C. chosen from monomers of formula $CH_2$=$CHCOOR_3$ are present in the block polymer in proportions by weight ranging from 10:90 to 20:80, wherein the intermediate block comprises at least one constituent monomer of the first block and at least one constituent monomer of the second block.

18. A block polymer comprising at least one first block, at least one second block, and an intermediate block linking the at least one first block and the at least one second block, wherein the first block consists essentially of at least one acrylate monomer of formula $CH_2$=$CH$—$COOR_2$ wherein $R_2$ is chosen from C4 to $C_{12}$ cycloalkyl groups and at least one methacrylate monomer of formula $CH_2$=$C(CH_3)$—$COOR'_2$ wherein R'2 is chosen from $C_4$ to $C_{12}$ cycloalkyl groups, and wherein the second block comprises at least one acrylic acid monomer and at least one monomer selected from isobutyl acrylate and 2-ethylhexyl acrylate, wherein the at least one acrylic acid monomer and the at least one monomer selected from isobutyl acrylate and 2-ethylhexyl acrylate are present in the block polymer in proportions by weight ranging from 10:90 to 20:80, wherein the intermediate block comprises at least one constituent monomer of the first block and at least one constituent monomer of the second block.

* * * * *